(12) United States Patent
Pospisilik et al.

(10) Patent No.: US 7,928,250 B2
(45) Date of Patent: Apr. 19, 2011

(54) PROCESS FOR MAKING DULOXETINE AND RELATED COMPOUNDS

(75) Inventors: Karel Pospisilik, Kritny (CZ); Bohumil Dymacek, Blansko (CZ)

(73) Assignee: Synthon BV, Nijmegen (NL)

( * ) Notice: Subject to any disclaimer, the term of this patent is extended or adjusted under 35 U.S.C. 154(b) by 719 days.

(21) Appl. No.: 12/004,294

(22) Filed: Dec. 20, 2007

(65) Prior Publication Data

US 2008/0171887 A1   Jul. 17, 2008

Related U.S. Application Data

(60) Provisional application No. 60/871,626, filed on Dec. 22, 2006.

(51) Int. Cl.
*C07D 333/12* (2006.01)
(52) U.S. Cl. ........................... 549/72
(58) Field of Classification Search ............ 549/72
See application file for complete search history.

(56) References Cited

U.S. PATENT DOCUMENTS

| | | |
|---|---|---|
| 5,362,886 A | 11/1994 | Berglund |
| 2003/0225153 A1 | 12/2003 | Eckert et al. |
| 2006/0167278 A1 | 7/2006 | Inoue et al. |

FOREIGN PATENT DOCUMENTS

| | | |
|---|---|---|
| EP | 0 273 658 A1 | 7/1988 |
| EP | 0 457 559 A2 | 11/1991 |
| EP | 0 693 282 A2 | 1/1996 |
| JP | 2004123596 | 4/2004 |
| WO | WO 00/61540 | 10/2000 |
| WO | WO 03/062219 A1 | 7/2003 |
| WO | WO 03/070720 A1 | 8/2003 |
| WO | WO 03/097632 A1 | 11/2003 |
| WO | WO 2004/005239 A1 | 1/2004 |
| WO | WO 2004/005307 A1 | 1/2004 |
| WO | WO 2004/013123 A1 | 2/2004 |
| WO | WO 2004/024708 A2 | 3/2004 |
| WO | WO 2004/031168 A2 | 4/2004 |
| WO | WO 2004/056795 A1 | 7/2004 |
| WO | WO 2004/065376 A1 | 8/2004 |
| WO | WO 2006/045255 A1 | 5/2006 |

*Primary Examiner* — Taofiq A Solola
(74) *Attorney, Agent, or Firm* — Muncy, Geissler, Olds & Lowe, PLLC

(57) ABSTRACT

A compound of formula 10 is useful in making duloxetine.

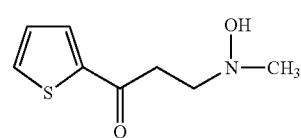

10

19 Claims, No Drawings

PROCESS FOR MAKING DULOXETINE AND RELATED COMPOUNDS

This application claims the benefit of priority under 35 U.S.C. §119(e) from U.S. provisional patent application Ser. No. 60/871,626, filed Dec. 22, 2006, the entire contents of which are incorporated herein by reference.

BACKGROUND OF THE INVENTION

The present invention relates to a process for making duloxetine and its related compounds as well as to intermediates useful therein.

Duloxetine is a pharmaceutically active compound useful as an antidepressant. Chemically duloxetine is S(+)-N-methyl-3-(1-naphthalenyloxy)-2-thiophenepropanamine of the formula (1a),

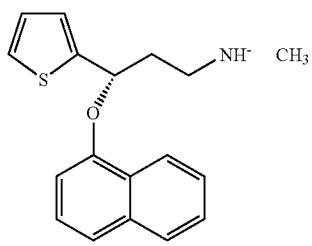

and is commonly used in pharmaceutical compositions as its hydrochloride salt. The marketed pharmaceutical dosage form of duloxetine, sold under such brand names as CYMBALTA®, is a capsule comprising a plurality of enteric coated pellets containing duloxetine hydrochloride. It is believed that the pharmaceutical formulation of the actually marketed pellets is covered by EP 693282 (U.S. Pat. No. 5,508,276) of Eli Lilly & Co.

EP 273,658 describes a variety of 3-aryloxy-3-substituted propanamines including duloxetine and the racemate thereof. The general reaction scheme can be represented as follows:

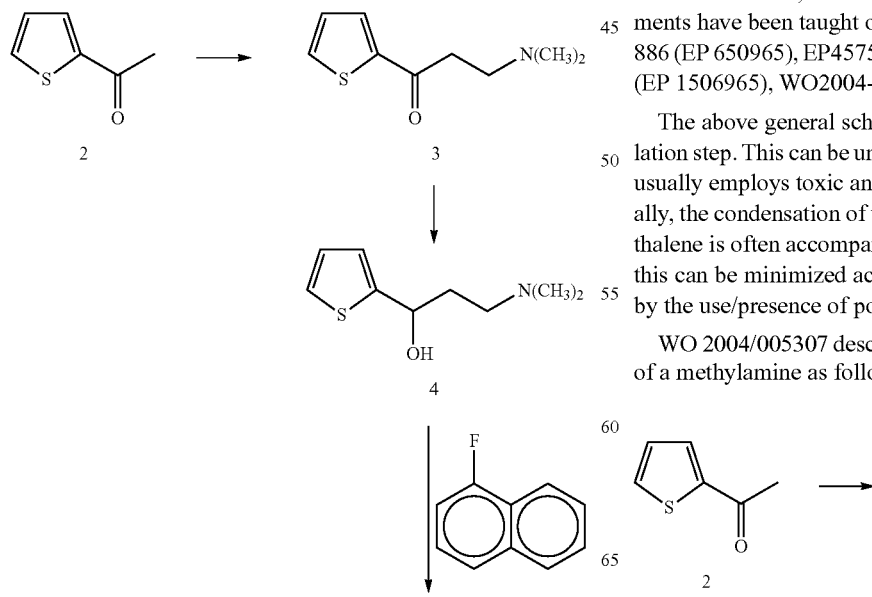

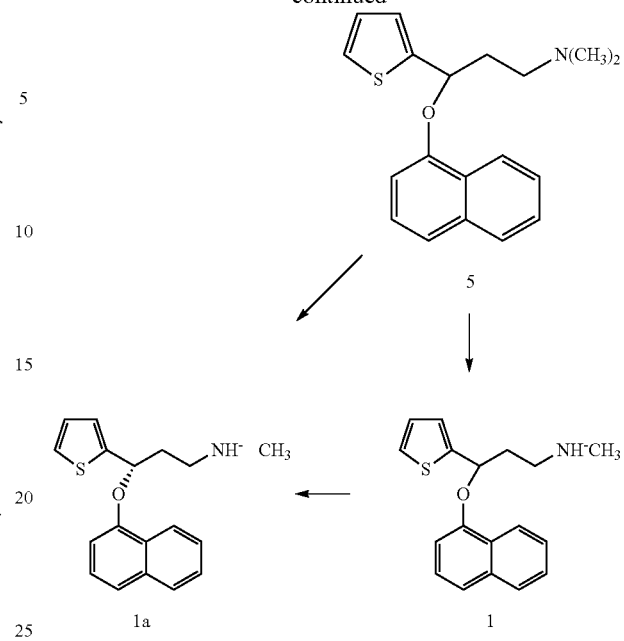

By Mannich reaction of 2-acetylthiophene 2 with paraformaldehyde and dimethylamine hydrochloride, the starting dimethylaminoketone 3 is obtained. The ketone 3 is reduced to the hydroxyl compound 4. The reduction can be stereo-specific, it can be racemic, or the racemate or mixture can be resolved. Thus, mixtures of the optical isomer as well as the pure or relatively pure optical isomer are contemplated by the above formula 4 and 5. After coupling with the fluoronaphthylene group, the compound is subjected to demethylation to form 1 or 1a if stereospecific intermediates were used. Alternatively, the racemate 1 can be resolved such as by a resolving agent, chromatography, etc., to form 1a, i.e., duloxetine. The synthesis was discussed in more detail in Deeter, et al., in Tetrahedron Letters, 31(49), 7101-04 (1990) and elaborations, variants, modifications and/or improvements have been taught or suggested in U.S. Pat. No. 5,362,886 (EP 650965), EP4575599 WO 00-061540, WO 03-97632 (EP 1506965), WO2004-056795 and WO 2006-045225.

The above general scheme, however, requires a demethylation step. This can be unattractive as the demethylation step usually employs toxic and irritating haloformates. Additionally, the condensation of the compound 4 with 1-fluoronaphthalene is often accompanied with a loss of chirality, though this can be minimized according to U.S. Pat. No. 5,362,886 by the use/presence of potassium compounds.

WO 2004/005307 describes forming duloxetine by the use of a methylamine as follows:

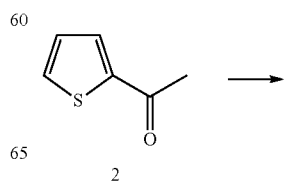

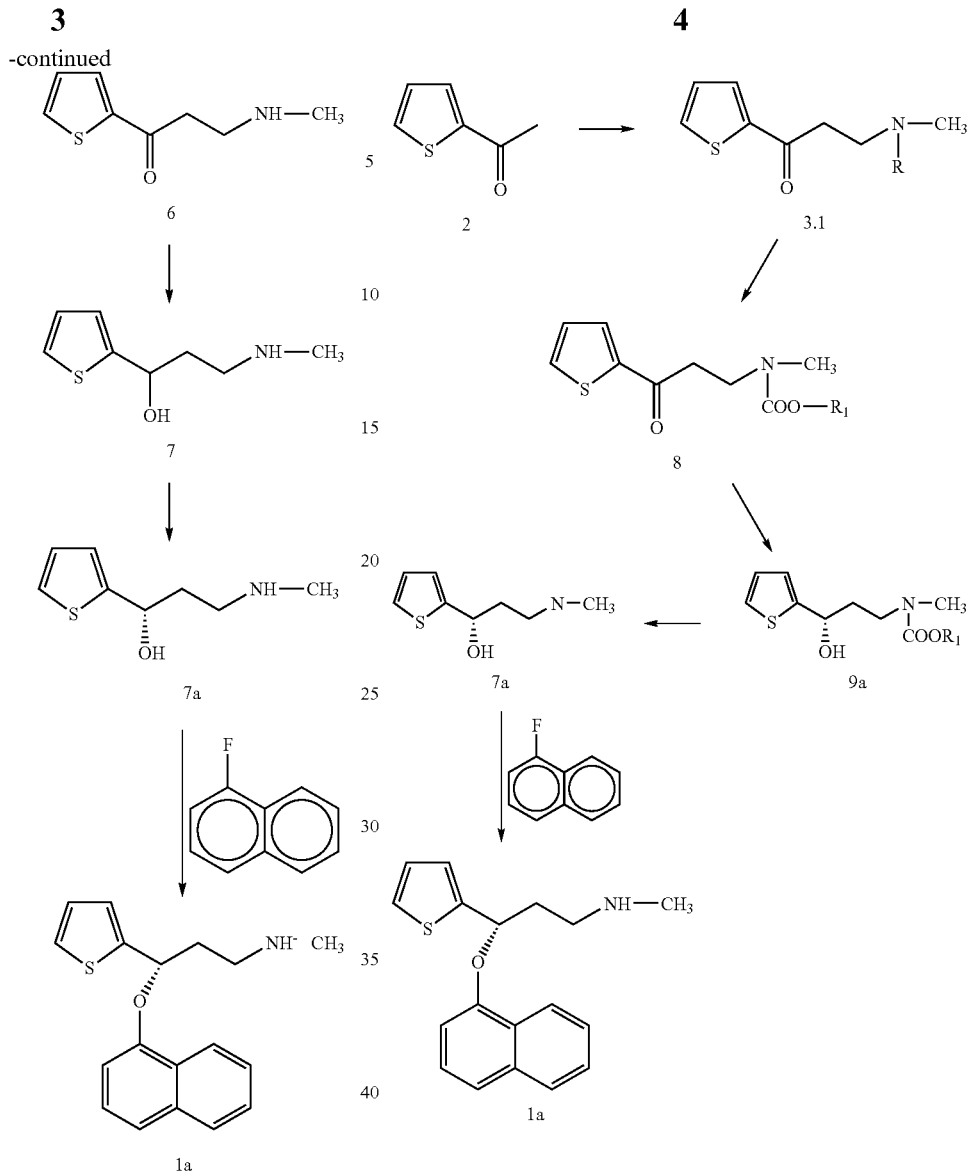

The resolving of the racemate 7 into the isomer 7a is specifically described. The compound 6 can be made by an analogous Mannich reaction as in the case of making the compound 3. Several other patents describe making or using such a compound (see WO 2004-031168, WO 2004-005307, WO 2004-005239, WO 2004-065376). But the preparation of 6 by Mannich reaction can be problematic as high levels of impurities can arise such as of the dimeric products (tertiary keto-amines). This is likely a result of the fact that the aminic nitrogen contains a hydrogen that is susceptible to side reactions. Moreover, the compound 6 is a relatively unstable compound, particularly in the form of free base. Therefore, reduction procedures leading to 7 and employing alkaline conditions run with a low yield and, when an attempt for the enantio-selective reduction is made, with a low selectivity.

WO 03-070720 describes another variant wherein a compound 3.1 is first converted to a keto-carbamate 8 and then reduced to the corresponding alcohol 9. The reduction can be stereospecific and/or the enantiomers can be resolved. The carbamate is subsequently hydrolysed to form 7 and then converted to duloxetine. In making duloxetine, the reaction can be represented as follows:

The preferred group R is a benzyl group. The Compound 2 is apparently an intermediate in the above-mentioned demethylation of 4 to 7. The process can thus suffer from the similar disadvantages as in other processes that use a demethylation step.

Additional processes for making duloxetine are disclosed in WO 2004-013123, US 2003-0225153, WO 2004-024708, in Chirality 2000, 12, 26-29, in Drugs of the Future 2000, 25(9), 907-916, and in Adv. Synth. Catal. 2003, 354, 261-274, WO 03-97632, WO 2004-005307, WO 03-062219, WO 03-070720, and JP 2004/123596.

Albeit many synthetic attempts were made, there is still a need for a convenient simple process for making duloxetine.

SUMMARY OF THE INVENTION

The present invention provides for a process for making duloxetine and related compounds that employs a convenient staring material and novel intermediates.

In a first aspect, the present invention provides for a compound of formula 10,

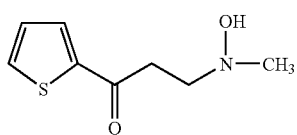

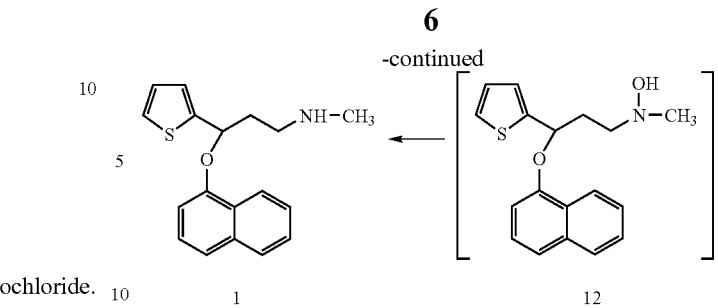

and acid addition salts thereof, particularly the hydrochloride.

Another aspect of the invention relates to a process of making the compound of formula 10 and/or acid addition salts thereof, comprising reacting the compound of formula 2 with N-methylhydroxylamine and formaldehyde according to the scheme

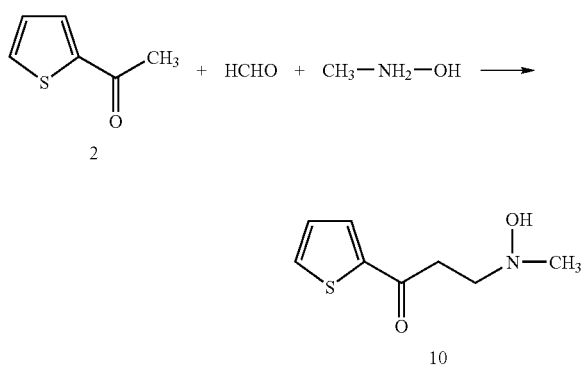

A further aspect of the invention relates to a process, wherein the compound 10 is converted into a compound of formula 1 or a pharmaceutically acceptable salt thereof. The conversion can be accomplished, for example, by any of the following pathways:

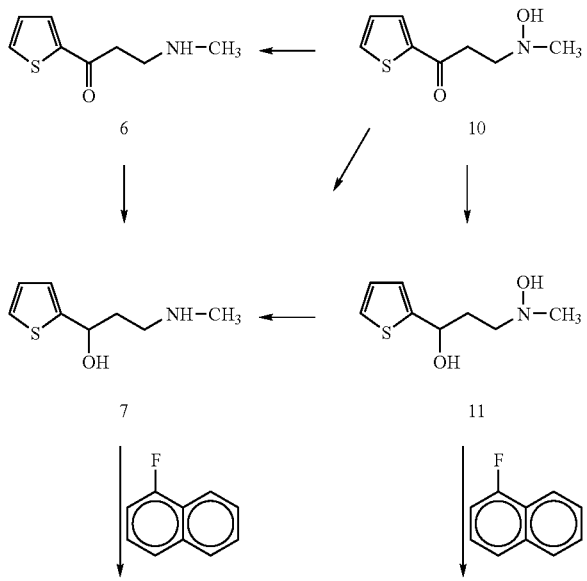

The compound 12 is shown in brackets because it can be converted in situ to compound 1 under typical condensation reaction conditions; e.g. from compound 11 to 1 in a single process step via compound 12. The compounds of 1, 7, 11, and 12 embrace racemates and the single R- or S-enantiomers, as well as mixtures of enantiomers. In any of compounds 7, 11, and 12 the S-enantiomer is advantageous so that duloxetine 1a is directly formed. Therefore, any of the synthetic steps, whenever it provides a racemate or a mixture of enantiomers, may be accompanied by a further step comprising the resolution of the racemate (or a mixture of enantiomers) into a single enantiomer. This includes the final step of forming compound 1; i.e. compound 1 can be resolved into 1a, if needed.

The intermediates 11 and 12, particularly the single enantiomers and most particularly the (S)-enantiomes thereof, and acid addition salts thereof, form another specific aspect of the invention.

DETAILED DESCRIPTION OF THE INVENTION

As used herein, all structural formulas include all possible spatial configurations unless otherwise specifically indicated. In particular, formulas that embrace two enantiomers include the racemic mixture as well as other mixtures of R and S forms and the individual R- and S-enantiomer. For clarity, the designation of a specific enantiomer, in either words or formula, means that that the compound is relatively enantiomerically pure, having no more than 10% of the other enantiomer, typically 5% or less, more typically 3% or less, and often 1% or less. In some embodiments, the single enantiomer, such as formula 1a, is desired to be highly pure having 0.5% or less, more preferably 0.2% or less and even 0.1% or less of the other enantiomer.

The present invention is based on the finding that the compound of formula 1 and particularly the (S)-enantiomer thereof, i.e. the duloxetine of formula 1a, may be prepared in a process employing the novel starting material of the formula 10.

The compound of formula 10 may be prepared by a simple reaction starting from the known compound of formula 2, whereby the yield and purity of the obtained product is generally higher than in an analogous process for making starting material 6. The presence of the hydroxy-group attached to the nitrogen atom minimizes side reactions on the nitrogen atom within further synthetic steps and, in comparison with the use of a second methyl group for the same purposes (as, for example, in the known intermediate 3), it may be removed, whenever desired, in a more convenient process.

The compound of formula 10 can be prepared by a condensation of the compound of formula 2 with N-methylhydroxylamine under the conditions of a Mannich reaction, i.e. under presence of formaldehyde and under acidic catalysis. Although chemical properties and reactivity of a hydroxylamine differ from those of the corresponding amine, it has been found that N-methyl hydroxylamine may be subjected to the Mannich reaction essentially under the same conditions as if the methylamine or dimethylamine were used. In general, lower temperatures are preferred for a successful course of the reaction. In a typical process, the acetylthiophene 2, formaldehyde (preferably paraformaldehyde) and N-methyl-hydroxylamine (preferably as the hydrochloride and/or with separately added acid, e.g. hydrochloric acid) react at 50-100° C. (suitably under reflux conditions) in a suitable solvent, e.g. in a lower alcohol such as ethanol.

The compound of formula 10 may be isolated from the reaction mixture in the form of an acid addition salt. The selection of the acid for forming such a salt is not particularly limited. Preferably, the compound is isolated as the hydrochloride salt, which can form a stable crystalline compound.

The acid addition salt, whenever prepared, may be converted to the free base of the compound 10 by a conventional neutralization reaction with a base in a suitable solvent, e.g. in water. The compound 10 is insoluble in water and may thus be isolated from an aqueous environment as a solid precipitate. Without any specific purification step, the compound of formula 10 may be thus obtained in a high purity, generally higher than 98% purity, and in very high yield. The free base of 10 is believed to be more stable in solid state than, e.g., the known compound 3.

The compound 10, including acid addition salts thereof (such as the hydrochloride) are suitable and advantageous starting materials for making the compounds of the general formula 1 and especially 1a, and salts thereof. It should be noted that, within the present invention, the structural formula 1 includes both the racemic compound and any single enantiomer thereof, particularly the duloxetine of formula 1a.

The compound 10 can be converted to the compound of the formula 1 or a salt thereof by a variety of pathways. Several variants are described below.

In the variant A, the compound 10 is converted to the known compound (6) by a removal of the hydroxy-group bound to nitrogen atom.

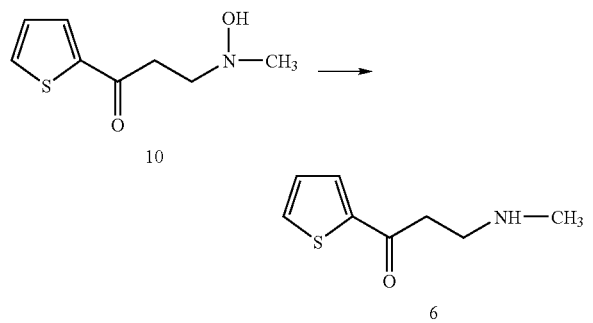

This may be done by a hydrogenolysis, e.g., by reacting the compound 10 with zinc or aluminium and an acid, preferably acetic acid, in an aqueous medium. The compound 6 may be isolated from the reaction mixture as a free base or as an acid addition salt.

In the next step(s), the compound 6 is further converted or "transformed" into the compound of formula 1, particularly to duloxetine of formula 1a, by known methods; e.g. reduction to 7 followed by condensation with a 1-halonaphthalene.

In a more preferred variant B, the compound 10 is first converted into a compound of the general formula 11.

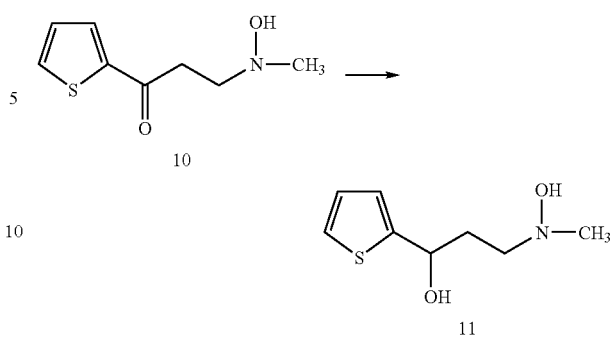

The formula 11 encompasses both the racemate compound and any single enantiomer thereof, particularly the S-enantiomer (S-11)

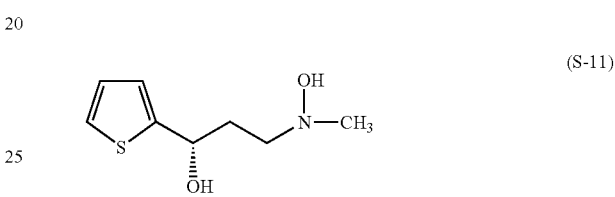

The compound of the general formula 11 may be made from the compound 10 by a reduction of the C=O double bond. Any useful reductive agent may be employed, for instance hydrogen in the presence of a hydrogenation catalyst, or a chemical reductant such as a diborane, a hydride, e.g., a borohydride such as sodium borohydride or an aluminium hydride, or zinc, etc. In general, the reduction process may either produce a racemic compound or the reduction may be enantio-selective, i.e. a single enantiomer of the compound 11 may be produced specifically or in a certain extent. If the racemate compound is produced, or if the reduction was not sufficiently enantio-specific, the reduction may be followed by resolution of the racemate into enantiomers; preferably with the aim of obtaining the S-enantiomer (S-11). A suitable resolution process comprises forming and resolving of a pair of diastereomeric salts made from chiral acids. Examples of the suitable chiral acids include tartaric acid, 0,0-dibenzoyl-tartaric acid, 0,0-ditoluoyltartaric acid, mandelic acid, camphorsulphonic acid, and diisopropylidene-2-ketogulonic acid, wherein any enantiomer of the chiral acid may be used. For example, the compound (S-11) may be obtained by the resolution of the compound (11) with 2,3:4,6-diisopropylidene-2-keto-L-gulonic acid.

In respect to the preferred final product of the overall process, the duloxetine of formula 1a, the compound 10 is preferentially reduced by an enantio-selective reduction yielding the single enantiomer, preferably the S-enantiomer of the formed alcohol 11. Various reduction processes that employ structurally similar starting materials 3 or 6 and that are more or less enantio-selective reduction processes are known in the prior art (e.g., WO 2004-031168; Angew. Chem. Int. Ed. 2005, 44, 1687-1689). These processes may be used analogously in the case of compound 10. More preferably, however, a new enantio-selective reduction process is used, which comprises carrying out reduction with a borane under catalysis of (R)-methyl-CBS-oxazaborolidine (=(R)-3,3-Diphenyl-1-methylpyrrolidino[1,2-c]-1,3,2-oxazaborole)

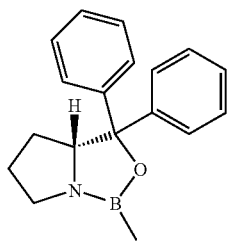

typically further in the presence of a Lewis acid. (R)-methyl-CBS-oxazaborolidine is a known and commercially available compound. To obtain sufficient enantioselectivity, it is advantageous to add at least a molar equivalent of a Lewis acid, which blocks the free electron pair of the hydroxylamine. A suitable Lewis acid is, e.g., trimethylborate. A suitable reaction solvent is tetrahydrofurane.

The compound (S-11) may be isolated by a conventional workup of the reaction mixture. If the enantiomeric purity of the isolated product is not sufficient for the next synthetic steps, it may be enhanced by forming a solution of a salt of the mixture of enantiomers of the formula 11 with an optically active acid and by precipitation of the desired S-enantiomer from said solution.

The above borane reduction may also be employed for making the reverse enantiomer of 11, (R-11), if the reduction is made under catalysis of (S)-methyl-CBS-oxazaborolidine.

The compound of formula 11, including the racemate, a mixture of enantiomers and the single enantiomer, may be isolated from the reaction mixture as a free base or as an acid addition salt, preferably in a solid state. The compound of general formula 11 may be converted into a compound of formula 1 by several routes.

For example, the hydroxy-group attached to the nitrogen in the compound 11 can be removed by hydrogenolysis to yield the compound 7.

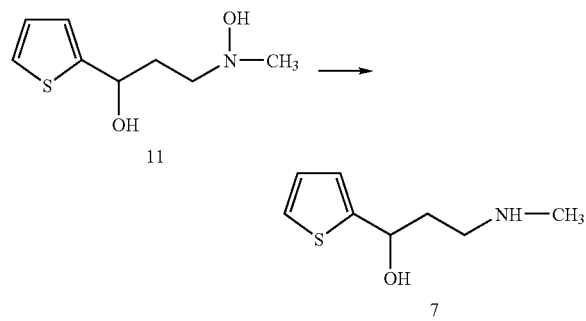

The hydrogenolysis is suitably performed by a native hydrogen formed, e.g., by the reaction of zinc with an acid. Acetic acid is the suitable acid and can serve also as a solvent for the reaction. In a preferred aspect, the single enantiomer of the compound 11, particularly the S-enantiomer of the formula (S-11), is advantageously used as the starting material, providing the single enantiomer of the compound of general formula 7 (compound (S-7) or (R-7)) substantially without racemization. Alternatively, the single enantiomer of compound 7 may be obtained by a resolution of the racemic compound 7, which may be produced by the above hydrogenolysis if the racemic starting material of the compound 11 is used. The resolution process is preferably based on resolution of a diastereomeric pair of salts with chiral acids and examples thereof are known from the prior art.

The compound of formula 7, including the racemate, mixture of enantiomers or a single enantiomer, may be isolated as a free base or as an acid addition salt, such as the hydrochloride or oxalate salt. The compound 7 is converted to the compound 1, particularly to duloxetine 1a, by known methods; e.g., condensation with a 1-halonaphthalene.

Alternatively, the compound of the formula 11 can be converted to a compound 1 via the compound of the general formula 12.

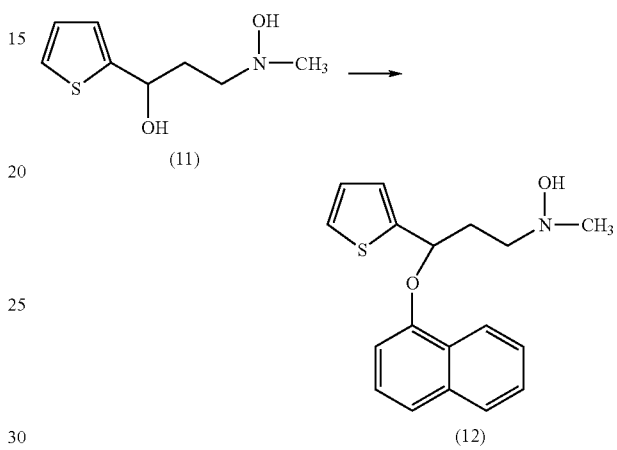

Dependent on the conformation of 11, the compound 12 may exist as a racemate compound or as a single enantiomer, e.g. the S-enantiomer of formula (S-12).

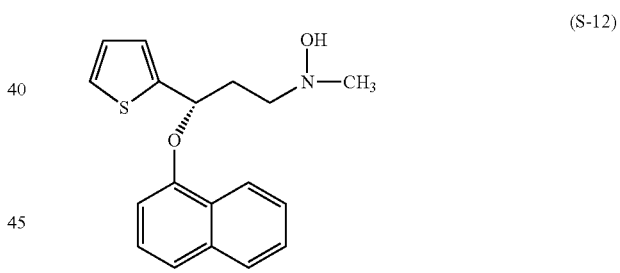

The compound of the general formula 12 may be obtained by the condensation of the compound of general formula 11 with a 1-halonaphthalene, particularly with 1-fluoronaphthalene. The reaction conditions can be similar to the conditions disclosed in the prior art in cases of the structurally similar starting materials of formula 5 or 7. The compound of the general formula 12 is then converted into the compound of formula 1 by a hydrogenolysis reaction.

It has been found that the two steps of condensation and subsequent hydrogenolysis can be carried out in a single process step. Under conventional conditions used in the prior art for making the duloxetine molecule, i.e., under condensation of the compound of general formula 11 with 1-fluoronaphthalene in the presence of sodium hydride, the OH— group is readily hydrogenolysed to yield the compound 1 without the need of isolation of compound 12 or any subsequent addition of further reagents. In this way, both the condensation of the naphthalene moiety and the removal of the protective OH— group are achieved in a single process step.

Such a procedure is the preferred use of compound 12, e.g., as a non-isolated intermediary. The compound 12 could, however, be isolated if desired.

When subjecting the single enantiomer of 11 (or 7) to condensation with a 1-halonaphthalene, it is preferable to carry out the condensation in the presence of a potassium salt in order to minimize racemization. This concept was identified in U.S. Pat. No. 5,362,886 using the dimethyl analogue of compound 7. Suitable potassium salts include potassium benzoate, potassium acetate, and potassium hexanoate.

In a third variant C, the compound 10 can be directly converted to the compound 7, i.e. the hydrogenolysis of the N—OH— group is performed in the same step as the reduction of the C=O bond. Subsequently, the compound 7 is converted to the compound of formula 1, and particularly to duloxetine of formula 1a, by known methods; e.g. condensation with 1-halonaphthalene.

Duloxetine of formula 1a may be isolated from the reaction mixture as a free base or as an acid addition salt, e.g. as duloxetine oxalate, optionally purified and converted, if desired into a pharmaceutically acceptable acid addition salt as described in the prior art. Typically the duloxetine is converted to duloxetine hydrochloride. When the conversion of 10 into 1 yields a racemate or other mixture of enantiomers, resolution may be further performed to obtain the S-enantiomer, namely duloxetine, via known resolution techniques.

The invention is further described by way of the following non-limiting examples.

EXAMPLE 1

Preparation of the Compound 10

A 50 ml bottle equipped with a reflux condenser, stirrer, nitrogen inlet tube was charged with 8.0 g of 2-acetylthiophene, 10 ml of ethanol, 7.5 g of N-methylhydroxylamine hydrochloride, 2.5 g of paraformaldehyde and 0.05 ml of 36% hydrochloric acid. The mixture was heated at reflux. All solid dissolved and after 3 hours the reaction mixture was diluted with 10 ml of ethanol, cooled in a refrigerator and mixed with 70 ml of acetone. The mixture was stirred for 30 min., solid was filtered off, the cake was washed with acetone and air dried to give 10.35 g of 10 hydrochloride.

5.1 g of 10 hydrochloride was dissolved in 10 ml of water and solution of 3.15 g of potassium carbonate in 10 ml of water was added. White crystals precipitated, they were filtered and the cake washed with water and air dried to give 3.7 g of 10 with HPLC purity 99.1% rel.

NMR confirmed the structure.

EXAMPLE 2

Preparation of the Racemic Compound 11

3.8 g of compound 10 was dissolved in 200 ml of ethanol, 0.74 g of sodium borohydride dissolved in 4 mL of alkalinized water was added and the mixture was stirred at ambient temperature for 16 h. Then 8 mL of acetone was added, mixture was stirred for 1 h and 20 mL of water was added. The mixture was twice extracted with 20 mL of ethylacetate. The combined ethylacetate extracts were washed with brine and concentrated in vacuo. Crystals precipitated on cooling, they were filtered off and air dried to give 2.5 g of a yellow solid product of the formula 11.

EXAMPLE 3

Preparation of the Compound 7

0.47 g of the compound 11 was dissolved in 6 ml of a mixture of glacial acetic acid and water (1:1 v/v) to form a slight yellow solution. Then 0.39 g of zinc was added and the reaction mixture was stirred at 50 C for 1 hour. Reaction mixture was cooled to ambient temperature, alkalinized with a 15% aqueous NaOH solution and evaporated to dryness. The solid was extracted with 20 ml of toluene. Combined toluene extracts were concentrated in vacuo, the residue dissolved in 3 ml of isopropanol and a solution of 0.22 g of oxalic acid in 1 ml isopropanol was added. The formed precipitate was filtered, the cake was washed with isopropanol and dried on air to give 0.39 g of the compound of formula 7, as oxalate.

EXAMPLE 4

Preparation of the Compound 1

2.5 g of the compound 11 was dissolved in a mixture of 50 ml of DMSO and 20 ml of tetrahydrofurane under nitrogen atmosphere. 1.40 g of 60% sodium hydride was added followed by addition of 0.27 g of potassium hexanoate. Reaction mixture was stirred at ambient temperature for 1 hour and 2.48 g of 1-fluoronaphthalene was added. The reaction mixture was heated at 60 C for 44 hours. Then the mixture was cooled, diluted with 50 ml of water and four times extracted with 30 ml of toluene. Combined toluene extracts were washed with 20 ml of brine. The toluene was removed in vacuo, the residue was dissolved in 20 ml of isopropanol and a solution of 1.3 g of oxalic acid in 10 ml of isopropanol was added. 50 ml of diisopropyl ether was added and the formed precipitate was filtered off and washed with diisopropyl ether to give, after drying, 2.35 g of the compound 1, as oxalate.

EXAMPLE 5

Preparation of the Compound (S-11)

0.80 mL of 1 M (R)-methyl-CBS-oxazaborolidine was dissolved in 12 mL of anhydrous tetrahydrofurane and 2.0 mL of 1.1 M borane-tetrahydrofuran complex was added. Solution was stirred for 1 h and then it was cooled on an ice bath. A solution of 3.3 g of the compound 10 and 3.2 g of trimethylborate dissolved in 24 mL of anhydrous tetrahydrofuran was added simultaneously with 24 mL of borane-tetrahydrofuran complex during 2 h. Reaction mixture was then stirred overnight at ambient temperature. The solvent was evaporated and the residue three times evaporated with 20 mL of methanol to give 5.5 g of oily residue. Part of this residue (0.70 g) was chromatographed on a column filled with silica gel eluted with 4% methanol in dichloromethane to get 0.38 g of yellow oily residue with $\alpha_D = -9.26°$ (c=0.82 in methanol).

EXAMPLE 6

Preparation of the Compound (R-11)

Under the conditions of the Example 5, with a proviso that the (S)-methyl-CBS-oxazaborolidine was used, 5 g of compound (R-11) was received from 8.1 g of the compound 10, with ee=88%.

EXAMPLE 7

Preparation of the Compound (S-7)

1.36 g of the compound (S-11) was dissolved in 40 ml of 50% acetic acid in water. 2.5 g of zinc was added and the mixture was stirred at 50° C. for 1.5 hour. Then the reaction mixture was filtered, filtrate alkalinized with 400 mL of 15% sodium hydroxide solution and received mixture five times extracted with 50 mL of ethylacetate. Combined ethylacetate extracts were washed with brine. Ethylacetate layer was concentrated in vacuo to give 3.5 g of residue, which was stirred with 50 mL of methanol, undissolved portion was filtered off and filtrate evaporated to dryness to give 1.25 g of oily residue. The yield was quantitative.

$\alpha_D = -12.8°$ (c=0.60 in methanol)

EXAMPLE 8

Preparation of the Compound (R-7)

Under conditions of the Example 7, 1.5 g of the compound (R-7) was received from 1.6 g of the compound (R-11), $\alpha_D = 13.1°$ (c=0.85, in methanol).

EXAMPLE 9

Preparation of (S)-Duloxetine Oxalate from (S-11)

2.3 g of the compound (S-11) were dissolved in 30 mL of DMSO and 12 mL of THF under nitrogene atmosphere. 0.84 g of potassium hexanoate was dissolved in the mixture followed by addition of 1.50 g of 60% sodium hydride. Reaction mixture was stirred at ambient temperature for 1 h and 2.5 g of 1-fluoronaphtalene was added. The reaction mixture was heated at 60° C. for 6 hours. Then the reaction mixture was cooled, diluted with 60 mL of water, and four times extracted with 20 mL of toluene. Toluene extracts were combined and washed with 30 mL of brine. Toluene was removed in vacuo, residue dissolved in 30 mL of isopropanol and solution of 1.5 g of oxalic acid was added. Precipitated solid was filtered off, washed with isopropanol and air dried to give 3.3 g of raw product. This product was dissolved in hot mixture of 50 mL of methanol and 1.6 mL of water. Crystals precipitated on cooling and were filtered off, washed with methanol and air dried to give 3.3 g of duloxetine oxalate with ee=85% (measured by HPLC). Structure of the product was confirmed by NMR.

EXAMPLE 10

Preparation of (R)-Duloxetine Oxalate from (R-11)

Under the conditions of Example 9, 1.6 g of (R)-Duloxetine oxalate was received from 2.5 g of R-11 with ee=87%

EXAMPLE 11

Preparation of (S)-Duloxetine Oxalate from (S-7)

2.24 g of the compound (S-7) was dissolved in 28 mL of DMSO and 4 mL of THF under nitrogene atmosphere. 1.0 g of potassium hexanoate was dissolved in the mixture followed by addition of 1.8 g of 60% sodium hydride. Reaction mixture was stirred at ambient temperature for 1 h and 2.9 g of 1-fluoronaphtalene was added. The reaction mixture was heated at 60° C. for 6 hours. Then the reaction mixture was cooled, diluted with 100 mL of water, and five times extracted with 50 mL of toluene. Toluene extracts were combined and washed with 30 mL of brine. Toluene was removed in vacuo, residue dissolved in 40 mL of isopropanol and 2.52 g of oxalic acid was added. Precipitated solid was filtered off, washed with isopropanol and air dried to give 3.5 g of raw product. This product was dissolved in hot mixture of 50 mL of methanol and 1.7 mL of water. Crystals precipitated on cooling and were filtered off, washed with methanol and air dried to give 3.1 g of duloxetine oxalate with ee=91% (measured by HPLC). Structure of the product was confirmed by NMR.

EXAMPLE 12

Preparation of (R)-Duloxetine Oxalate from (R-7)

Under conditions of the Example 11, 1.1 g of (R)-Duloxetine oxalate was received from 1.4 g of (R-7) with ee=96%

EXAMPLE 13

Resolution of Compound 11

11.4 g of the compound 11 was dissolved in 66 ml of acetone and 15.9 g of 2,3:4,6-diisopropylidene-2-keto-L-gulonic acid was added. The reaction mixture was stirred and then placed into a refrigerator for 72 hours. The white precipitate was filtered off and the filtrate was evaporated in vacuo. The residue was dissolved in water, 10 ml of ammonia was added and the mixture was extracted three times with 20 ml of dichloromethane. Combined dichloromethane extracts were washed with brine and evaporated to give 4 g of a product.

Each of the patents, patent applications, and journal articles mentioned above are incorporated herein by reference in there entirety. The invention having been described it will be obvious that the same may be varied in many ways and all such modifications are contemplated as being within the scope of the invention as defined by the following claims.

What is claimed:

1. A compound of formula 10

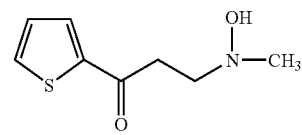

or an acid addition salt thereof.

2. A compound selected from the group consisting of formulas 11 and 12

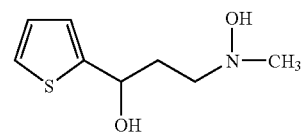

-continued

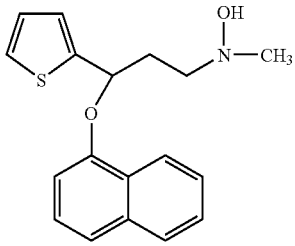

and acid addition salts thereof.

3. The compound according to claim 2, which is the S-enantiomer of a compound of formula 11 or an acid addition salt thereof.

4. A process, which comprises converting a compound of formula 10 or an acid addition salt thereof

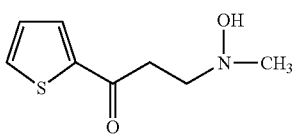

into a compound of formula 1

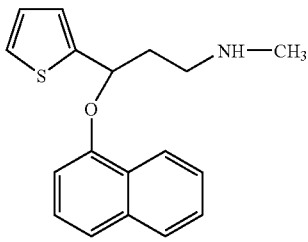

or a pharmaceutically acceptable salt thereof.

5. The process according to claim 4, wherein said converting step comprises reducing said compound of formula 10 or salt thereof to form a compound of formula 11

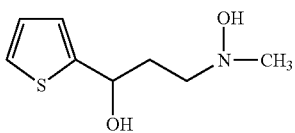

or an acid addition salt thereof.

6. The process according to claim 5, wherein said reduction is an enantio-selective reduction process which provides the S-enantiomer of the compound of formula 11 or the salt thereof.

7. The process according to claim 6, wherein said enantio-selective reduction process is carried out with a borane under catalysis of (R)-methyl-CBS-oxazaborolidine and in the presence of a Lewis acid.

8. The process according to claim 7, wherein said Lewis acid is trimethylborate.

9. The process according to claim 7, wherein said enantio-selective reduction process is carried out in a solvent comprising or consisting of tetrahydrofurane.

10. The process according to claim 6, wherein said converting step further comprises condensing said S-enantiomer of the compound of formula 11 with a 1-fluoronaphthalene compound in the presence of sodium hydride and optionally a potassium compound, to form said compound of formula 1 as a compound of formula 1a

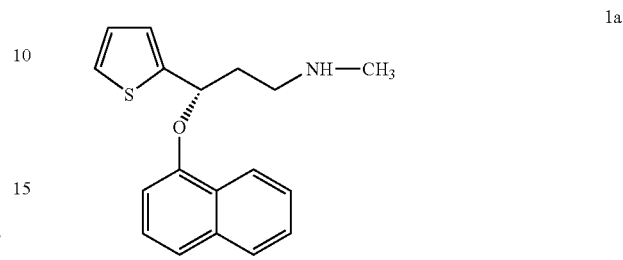

or a pharmaceutically acceptable salt thereof.

11. The process according claim 10, wherein said converting step produces said compound of formula 1 as a mixture of enantiomers.

12. The process according to claim 11, which further comprises resolving said mixture of enantiomers to obtain a compound of formula 1a

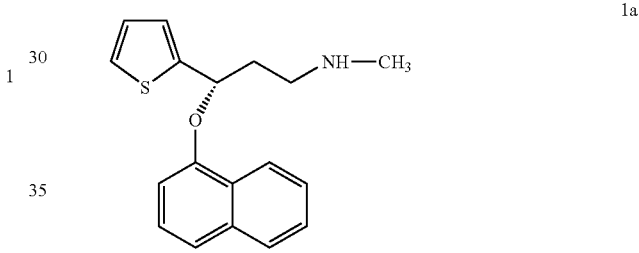

or a pharmaceutically acceptable salt thereof.

13. The process according to claim 5, wherein said converting step further comprises
subjecting said compound of formula 11 to hydrogenolysis to form a compound of formula 7

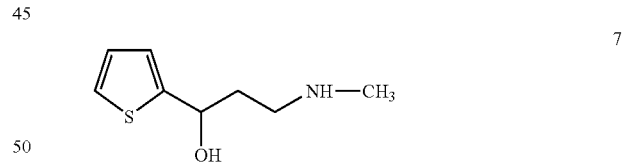

or a salt thereof; and
condensing said compound of formula 7 with a 1-fluoronaphthalene compound to form said compound of formula 1.

14. The process according to claim 4, wherein said converting step comprises reducing said compound of formula 10 to form a compound of formula 6

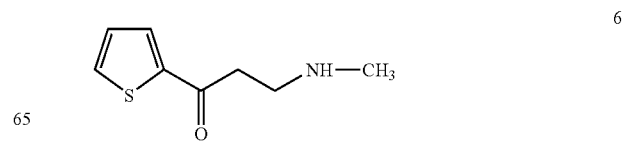

or a salt thereof and transforming said compound of formula 6 into said compound of formula 1.

15. The process according to claim 4, which further comprises reacting acetylthiophene of formula 2

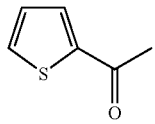

2 with formaldehyde and N-hydroxymethylamine to form said compound of formula 10.

16. A process, which comprises reacting an acetylthiophene of formula 2

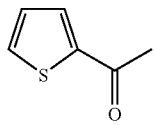

2 with formaldehyde and N-hydroxymethylamine to form a compound of formula 10

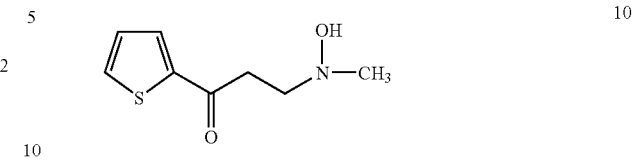

10 or an acid addition salt thereof.

17. The process according to claim 16, wherein the compound 10 is isolated from the reaction mixture in solid state.

18. The process according to claim 17, wherein the compound 10 is isolated as a hydrochloride.

19. The process according to claim 5, wherein said converting step further comprises condensing said compound of formula 11 with a 1-fluoronaphthalene compound in the presence of sodium hydride to form said compound of formula 1 or salt thereof.

* * * * *